(12) United States Patent
Bojarski et al.

(10) Patent No.: US 6,533,802 B2
(45) Date of Patent: Mar. 18, 2003

(54) ENDOBUTTON CONTINUOUS LOOP FOR BONE-TENDON-BONE

(75) Inventors: Raymond A. Bojarski, Attleboro, MA (US); Paul A. Torrie, Marblehead, MA (US); Stuart E. Fromm, Rapid City, SD (US)

(73) Assignee: Smith & Nephew, Inc., Memphis, TN (US)

( * ) Notice: Subject to any disclaimer, the term of this patent is extended or adjusted under 35 U.S.C. 154(b) by 48 days.

(21) Appl. No.: 09/859,096

(22) Filed: May 16, 2001

(65) Prior Publication Data

US 2002/0173788 A1 Nov. 21, 2002

(51) Int. Cl.[7] .............................. A61B 17/04; A61F 2/08
(52) U.S. Cl. ...................... 606/232; 606/228; 623/13.11
(58) Field of Search .................... 606/232, 72, 228; 623/13.11, 13.2

(56) References Cited

U.S. PATENT DOCUMENTS

| 3,880,166 A | | 4/1975 | Fogarty | |
|---|---|---|---|---|
| 5,306,301 A | * | 4/1994 | Graf et al. | 606/72 |
| 5,645,588 A | * | 7/1997 | Graf et al. | 606/151 |
| 5,733,289 A | | 3/1998 | Seedhom et al. | 606/80 |
| 5,769,894 A | | 6/1998 | Ferragamo | 623/13 |
| 6,056,752 A | | 5/2000 | Roger | 606/72 |
| 6,086,591 A | | 7/2000 | Bojarski | |

FOREIGN PATENT DOCUMENTS

| EP | 0 598 219 A2 | 5/1994 | |
|---|---|---|---|
| WO | WO 98/12991 | 4/1998 | A61F/2/08 |
| WO | WO 99/47079 | 9/1999 | A61F/2/08 |
| WO | WO 02/32345 A2 | 4/2002 | |

* cited by examiner

Primary Examiner—Gregory Huson
Assistant Examiner—Lina R Kontos
(74) Attorney, Agent, or Firm—Fish & Richardson P.C.

(57) ABSTRACT

A method of securing a tissue graft within a bone passage includes providing a graft fixation member comprising a closed-loop having a pair of opposing loop sections and capturing a first loop section of the closed-loop within the fixation member. An opposing second loop section of the closed loop is passed through an opening in the tissue graft, and the second loop section of the closed loop is secured to the fixation member.

37 Claims, 16 Drawing Sheets

ENDOBUTTON CONTINUOUS LOOP FOR BONE-TENDON-BONE

TECHNICAL FIELD

This invention relates to anchoring tissue grafts.

BACKGROUND

An increasing number of surgical techniques are now performed arthroscopically. One type of arthroscopic procedure reconstructs the anterior cruciate ligament (ACL) in the knee. Several ACL reconstruction techniques are described in U.S. Pat. No. 5,139,520 (issued Aug. 18, 1992) ("the '520 patent") and incorporated by reference.

When the ACL has ruptured and is nonrepairable, it is usually replaced in the knee using a substitute graft harvested from the patient or from a donor. The substitute ACL graft may be a portion of a patellar tendon having so called "bone blocks" at each end. A method and an apparatus for harvesting such a patellar tendon graft is described in U.S. Pat. No. 5,733,289 (issued Mar. 31, 1998) ("the '289 patent") and incorporated by reference. Alternatively, an artificial graft formed from synthetic materials or from a combination of artificial and natural materials may be used and is sometimes referred to as a ligament augmentation device (LAD). The term "tissue graft" is used herein to encompass all of these tissue replacement items.

In general, the replacement tissue graft is implanted by securing one end of the tissue graft in a socket formed in a passage formed within the femur (i.e., femoral channel) and passing the other end of the graft through a passage formed in the tibia (i.e., tibial channel). Then, the graft is secured to the tibia adjacent to the tibial channel. Generally, sutures are used to affix each end of the tissue graft to a fastener (e.g., an interference screw or a post), which is then secured to the bone. Descriptions of these fasteners and methods of forming the passages through the tibia and femur are described in greater detail in the '520 patent.

Another approach for affixing a tissue graft is described in U.S. Pat. No. 5,306,301, (issued Apr. 26, 1994) ("the '301 patent") and incorporated by reference. The '301 patent discloses using a fixation button to secure a tissue graft at the femoral cortex. The fixation button has an elongated shape and at least one pair of openings through which a suture may be passed and then tied off.

In this approach, the femoral channel has a portion having a first diameter sized to accommodate a bone block and a second portion having a smaller diameter through which the bone block cannot pass. By measuring the total length of the femoral channel and the length of the larger portion, the surgeon determines a "suture span" for attaching the fixation button to the tissue graft.

The surgeon forms an opening in the bone block to be positioned in the femoral channel and threads an end of suture through it. The surgeon then ties the suture to the fixation button, providing the suture span between the button and the bone block. The fixation button and the tissue graft are then passed through the tibial and femoral channels until the graft is properly seated within the socket portion of the femoral passage and the fixation button is firmly seated against the femoral cortex. The tissue graft is then tensioned and anchored at its opposite end using a fixation screw secured within the tibia.

Still another approach for affixing a tissue graft is described in U.S. Pat. No. 5,769,894, (issued Jun. 23, 1998) ("the '894 patent") and incorporated by reference. The '894 patent describes a graft fixation member configured to allow the length of the suture between the fixation member and the graft to be adjusted and to maintain the adjusted length when the suture is secured to the graft fixation member.

An alternative to tying a suture to a fixation button is disclosed in PCT Application WO 99/47079 (published Sep. 23, 1999) ("the '079 application") and incorporated by reference. The '079 application discloses an apparatus and method for attaching a continuous loop of suture to a fixation button. Using a series of rollers, the continuous loop is formed from a strand of suture repeatedly coiling the suture through openings in a fixation button. In other examples, a continuous loop of suture may be formed without a fixation member. Continuous loops, both with and without fixation buttons attached, are available from Xiros Limited, Leeds, England, in several sizes. A surgeon selects the closest matching size for a given ACL reconstruction procedure. In other examples, a continuous loop of suture may be formed without a fixation member.

SUMMARY

In an aspect, the invention features a method for securing a tissue graft within a bone passage. A graft fixation member comprising a closed-loop having a pair of opposing loop sections is provided and a first loop section of the closed loop is captured within the fixation member. An opposing second loop section of the closed loop is passed through an opening in the tissue graft and is secured to the fixation member.

In another aspect, the invention features a method of securing a tissue graft within a bone passage including providing a graft fixation member comprising a closed loop having a pair of opposing loop sections. A first loop section of the closed loop is captured within the fixation member. A bight is formed in the closed loop by passing an opposing second loop section of the closed loop through an opening in the tissue graft. The fixation member and the first loop section are passed through the bight in the closed loop to capture the tissue graft.

In another aspect, the invention features a method of securing a tissue graft within a bone passage including providing a first graft fixation member and a second graft fixation member and a closed loop having a pair of opposing loop sections. A first loop section of the closed loop is captured within the first graft fixation member and an opposing second loop section is passed through an opening in the tissue graft. A second loop section of the closed loop of suture is captured within the second graft fixation member.

One or more of the following features may also be included. The opening is formed in the tissue graft. The opening is formed in a bone block of the tissue graft. The opening is formed in a tendon of the tissue graft. The fixation member is passed through the bone passage. The fixation member through a bone passage in a tibia and then through a bone passage in a femur. The fixation member is first passed through a bone passage in a femur and then through a bone passage in a tibia. The fixation member is positioned to pass through the bone passage using a suture. The fixation member is positioned to pass through the bone passage using closure tape. The second loop section is captured within the second fixation member before the second loop section is passed through the opening in the tissue graft. Passing the second loop section through the opening in the tissue graft includes passing the second fixation member through the opening.

In another aspect, the invention features a device for securing a tissue graft within a passage within a bone. The device includes a member having an intermediate portion and an end portion. The end portion has a pair of arms extending from the intermediate portion and defining an open channel at the end portion. Each arm has an opening extending from a first side of the arm to a second side of the arm, the opening being sized to accommodate a strand of suture.

One or more of the following features may also be included. One or more openings pass through the intermediate portion of the member. The openings are cylindrical. The opening in each arm is cylindrical. The openings in each pair of arms occupy different positions on a common axis. The axis is transverse to the member. The pair of arms define a cylindrical portion of the channel having a diameter equal to the width of the channel. Each pair of arms define a cylindrical portion of the channel having a diameter greater than the width of the channel. The arms are shaped to pass through bone passage. The member is sized to pass through a bone passage. The member comprises a bio-compatible material. The member comprises titanium. The member comprises a bio-absorbable material.

Embodiments may have one or more of the following advantages. The closed loop may be manufactured and purchased separate from the fixation member. This allows the surgeon the flexibility to choose the correct size closed loop from several sizes available in the operating room without a fixation member on each size loop. In turn, the patient benefits from the reliability of the closed loop without the added cost of multiple fixation members. The closed loop is positively captured within the fixation member during implantation. The closed loop provides superior strength over single loops of tied suture or tape and does not extend a patient's time under anesthesia while a surgeon forms multiple loops of suture or tape by hand. The closed loop may be pre-stressed during the manufacturing process to reduce its elasticity and increase its strength without accommodation for a fixation member.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
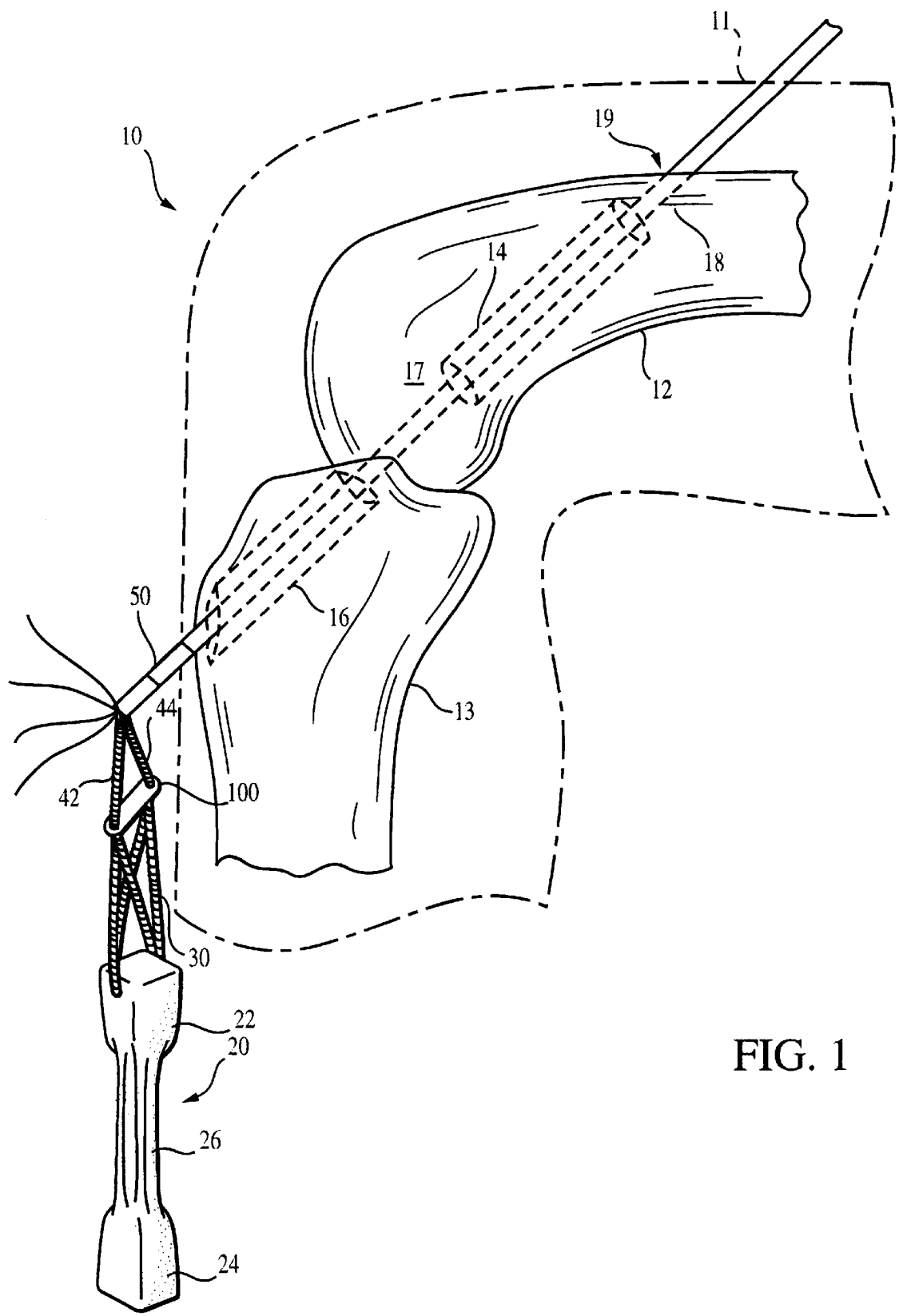
FIG. 1 shows an example of a tissue graft being implanted during an ACL reconstruction procedure using a closed-loop suture and a graft fixation member.

Referring to FIG. 1, a tissue graft 20 is shown being implanted within a knee 10 during an anterior cruciate ligament (ACL) repair and reconstruction procedure. In one example, tissue graft 20 has bone blocks on both ends sized and shaped to fit within femoral and tibial channels, respectively. More specifically, one end of tissue graft 20 includes a bone block 22 shaped and sized in substantial conformity with a femoral channel 14 of femur 12 while the other end of tissue graft 20 includes a bone block 24 shaped and sized in substantial conformity with tibial channel 16 of tibia 13. In one example, a closed-loop suture 30 is inserted into bone block 24 and captured within graft fixation member 100. Closed-loop suture 30 could be, but is not limited to, a Smith & Nephew continuous loop made from polyester, a strand of suture tied in a loop, or a piece of polyester closure tape (e.g., Merselene™ from Ethicon Inc., Cincinnati, Ohio) tied in a loop. As will be described below, graft fixation member 100 is configured to facilitate positioning and securing the tissue graft 20.

Sutures 42 and 44 extend through fixation member 100 and are removably attached to passing pin 50 which is used to draw the sutures 42, 44 through the tibial channel 16, femoral channel 14, and passing channel 18. As described below, sutures 42, 44 are used to pull graft fixation member 100 through passing channel 18 and position tissue graft 20 within femoral channel 14 and tibial channel 16.

Figure 2:
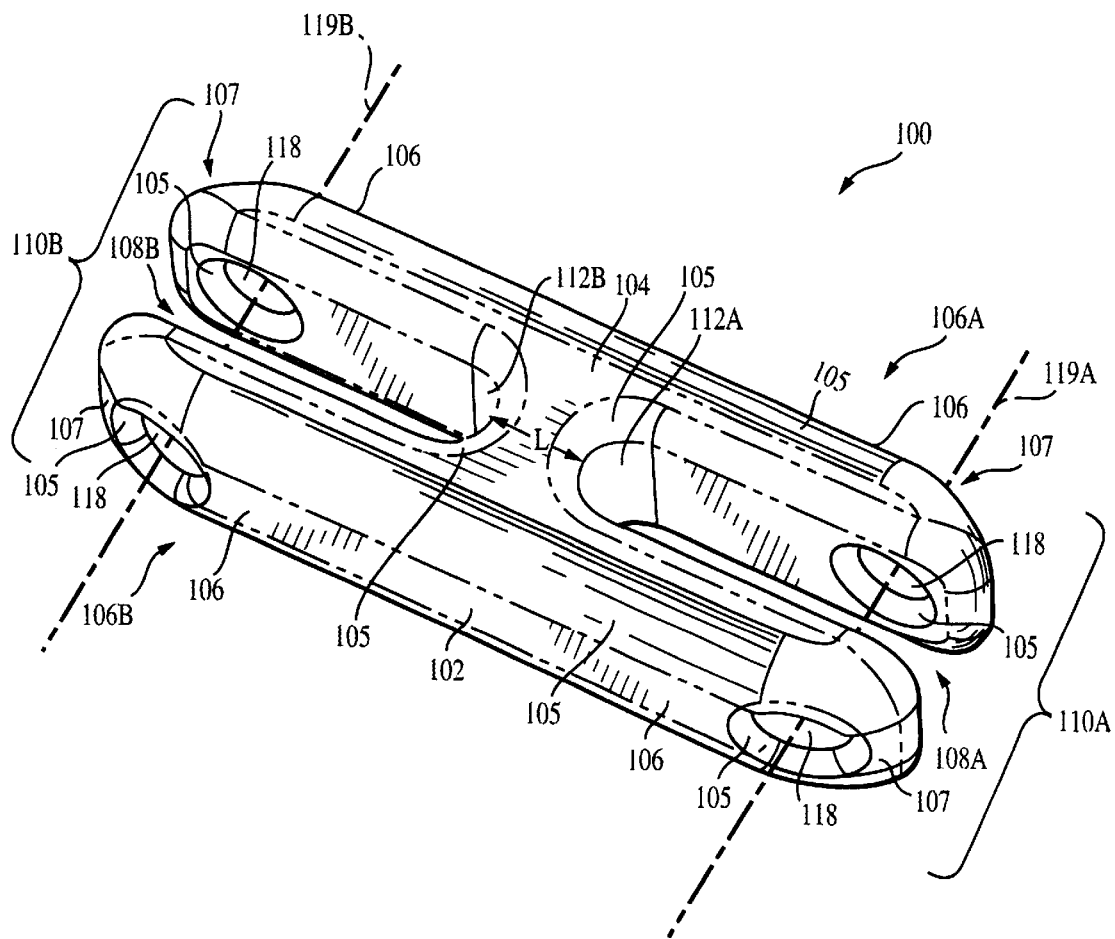
FIG. 2 is an example of the graft fixation member.

In one example, shown in FIG. 2, in one example graft fixation member 100 has an elongated body 102 formed of a biocompatible material (e.g., titanium or acetal) or a bioabsorbable material (e.g., polylactic acid, polyglycolic acid) with a length of about 0.45 inches, a width of about 0.16 inches, and a thickness of about 0.1 inches. Body 102 has a width allowing fixation member 100 to be pulled through tibial channel 16, femoral channel 14, and passing channel 18.

Body 102 includes an intermediate portion 104 having a length (L), which defines the distance between a pair of channels 108A, 108B at opposing ends of body 102, described below. In one example, length (L) of intermediate portion 104 is about 0.05 inches. Intermediate portion 104 supports closed-loop suture 30 during implantation and bears the tension of closed-loop suture 30 after tissue graft 20 has been implanted.

Pairs of arms 106A and 106B extend from intermediate portion 104. Arms 106 have rounded edges 105 along their length and rounded ends 107. In one example, rounded edges 105 have a radius of about 0.015 inches and rounded ends 107 have a radius of about 0.067 inches. Rounded edges 105 allow fixation member 100 to be more easily pulled through tibial channel 16, femoral channel 14, and passing channel 18.

Channels 108A and 108B are formed by pairs of arms 106A and 106B, respectively. Channels 108A and 108B are open at end portions 110A and 110B of elongated body 102 and have cylindrical closed portions 112A and 112B formed by intermediate portion 104 and pairs of arms 106A and 106B, respectively. For example, cylindrical closed portions 112A and 112B could have a diameter of about 0.05 inches and channels 108 and 108B could have a corresponding width of about 0.05 inches. Open end portions 110A and 110B of channels 108A and 108B allow closed-loop suture 30 to pass into channels 108A and 108B as described below.

In this particular embodiment, each arm 106 has an opening 118 located toward the end of and extending through arm 106. Openings 118 are cylindrical and have a diameter of about 0.04 inches. Openings 118 in pair of arms 106A are disposed on a common axis 119A, which is transverse to the length of elongated member 102. Openings 118 in pair of arms 106B are disposed on a common axis 119B, which is also transverse to the length of elongated member 102. In other examples, openings 118 could be skewed in relation to each other or disposed at different positions along arms 106.

Figure 3:
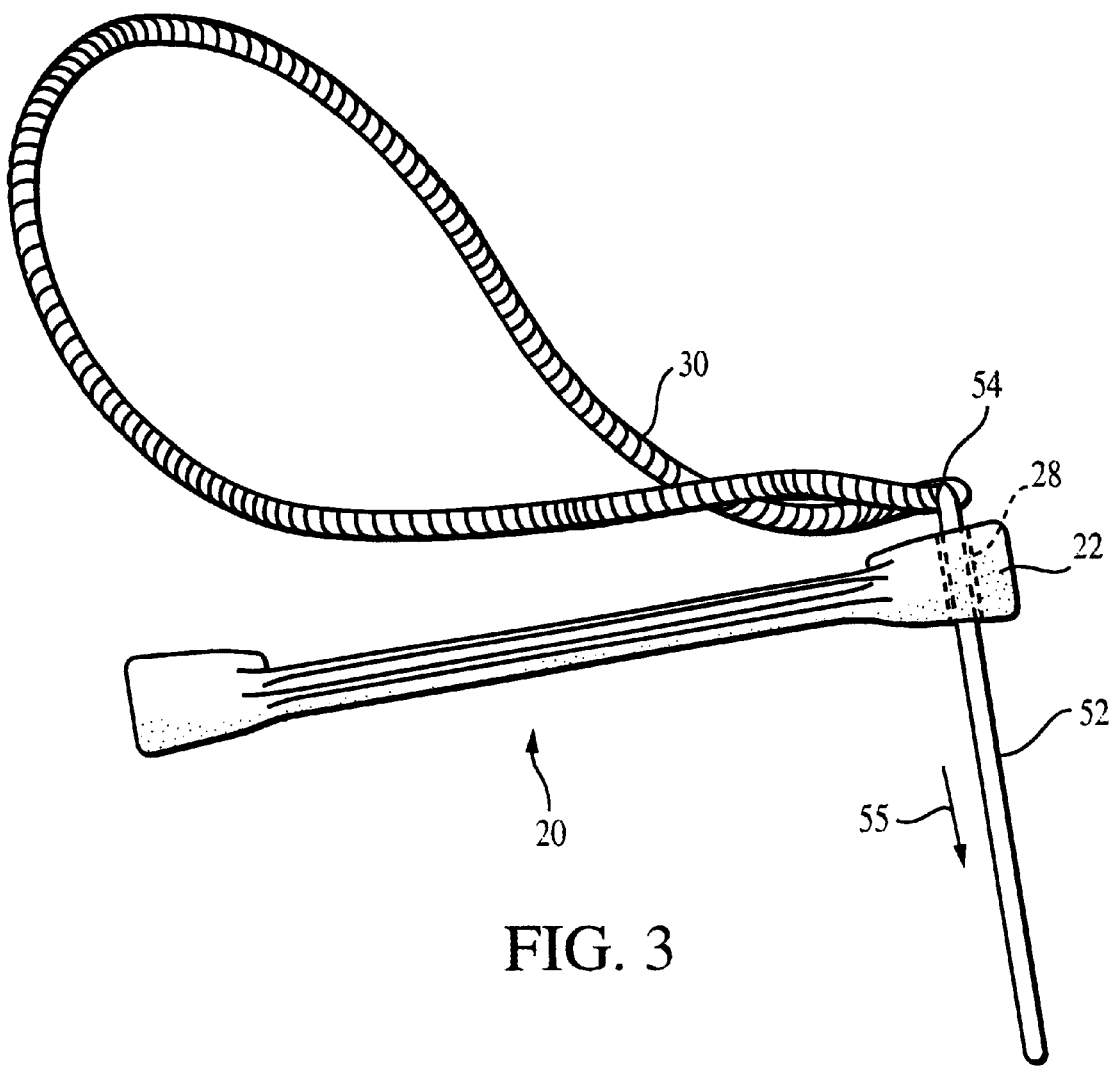
FIG. 3 shows an exploded partial view of how closed-loop suture could be inserted into tissue graft.
Figure 4:
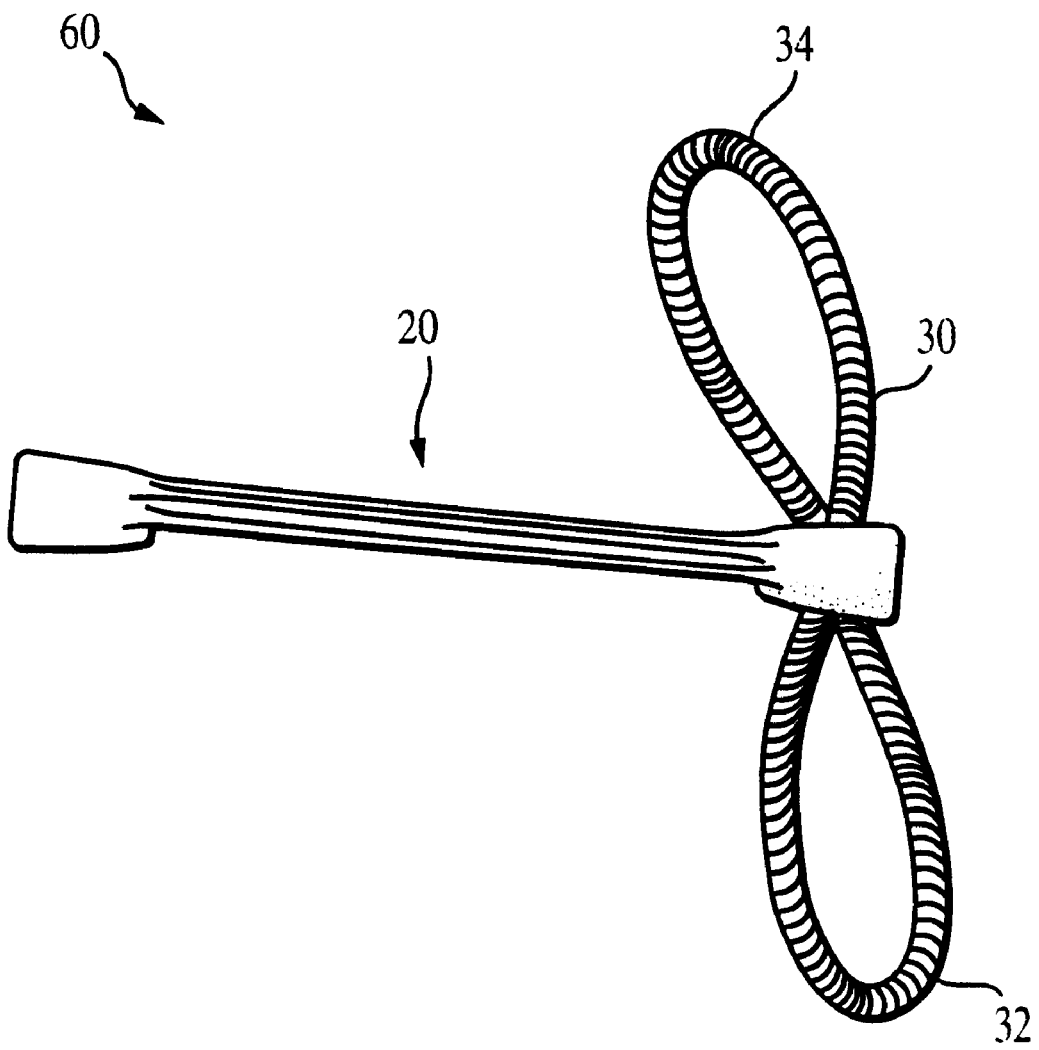
FIG. 4 is an example of a graft-loop assembly before being attached to the graft fixation member.

Referring to FIGS. 3–7, an example of a procedure for attaching graft fixation member 100 to tissue graft 20 follows. Referring to FIGS. 3 and 4, opening 28 is formed, for example, by drilling through bone block 22. A surgeon chooses a closed-loop suture 30 from closed loops of several lengths to best position the tissue graft 20 within femoral channel 14 and tibial channel 16 (FIG. 1). The surgeon inserts suture grabber 52 into opening 28 until the end 54 of device 52 extends from bone block 22 and positions closed-loop suture 30 next to bone block 22. The surgeon grabs closed-loop suture 30 with suture grabber 52 and pulls both back through opening 28 in direction 62, forming a first bight 32 and a second bight 34 of about the same size on either side of bone block 22. Alternatively, a length of suture (not shown) could be used to pull closed-loop suture 30 into opening 28. One end of the suture could be passed through opening 28, through closed-loop suture 30, and back through opening 28. Closed-loop 30 may then be positioned in opening 28 by pulling both ends of the strand of suture.

Figure 5:
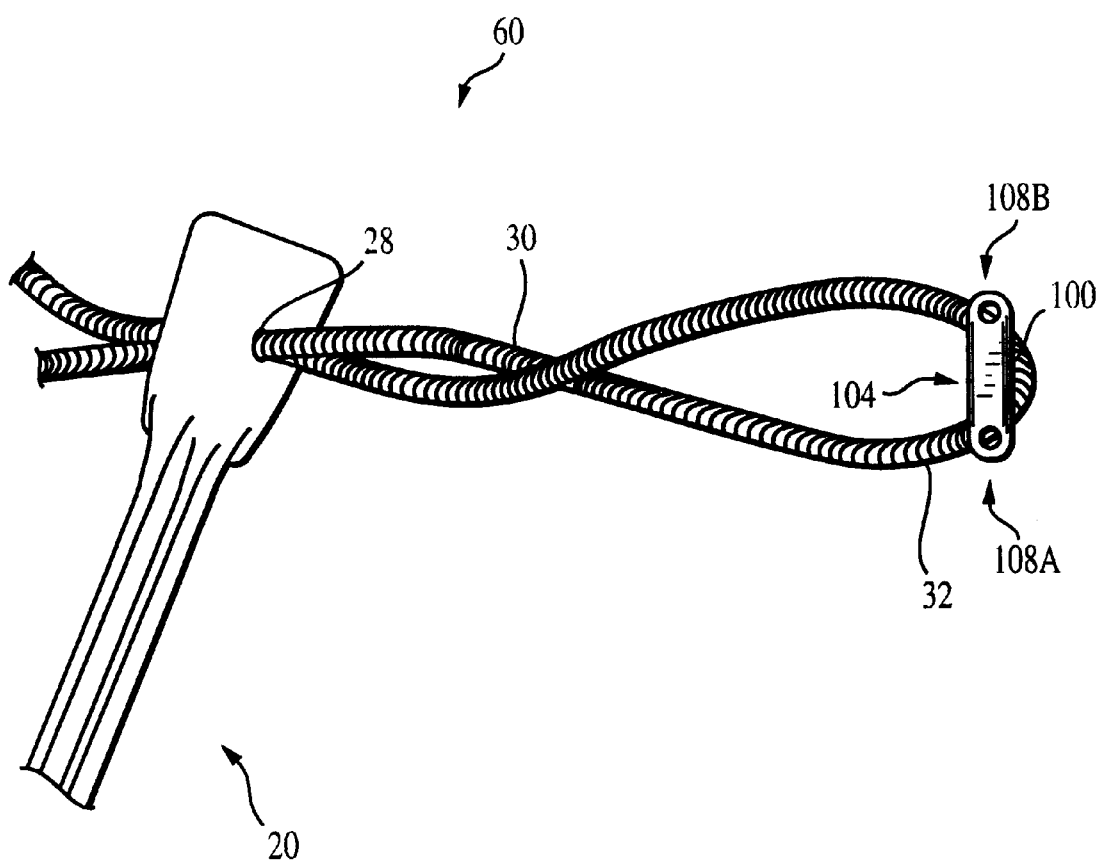
FIG. 5 shows an exploded partial view of a graft-loop assembly partially captured by the graft fixation member.
Figure 6:
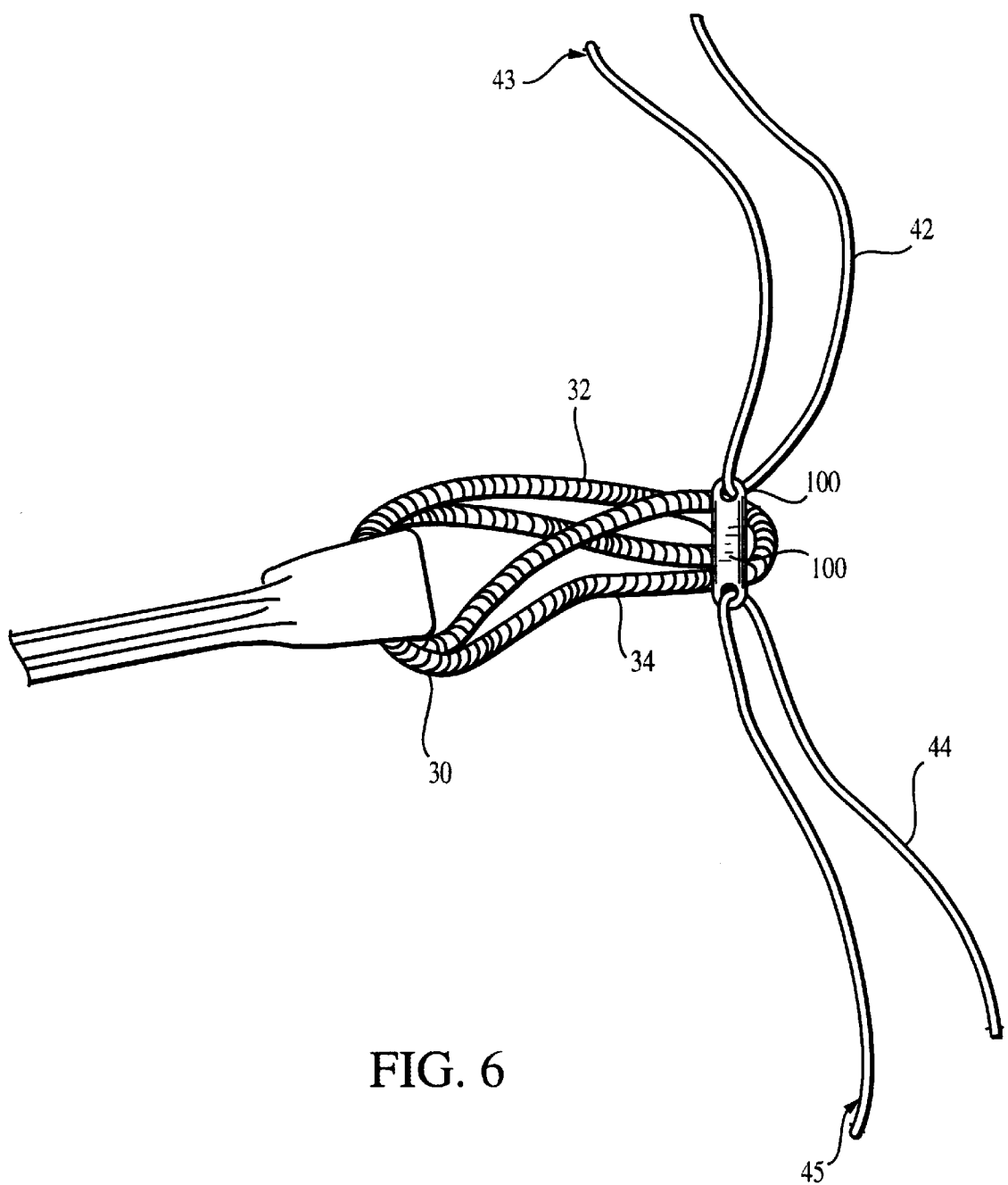
FIG. 6 shows an exploded partial view of a graft-loop assembly fully captured by the graft fixation member.

Referring to FIGS. 5 and 6, bight 32 is positioned around graft fixation member 100 and ##into channels 108A, 108B so that the continuous loop of suture 30 is wrapped around intermediate portion 104 of graft fixation member 100. Bight 34 of continuous loop of suture 30 is then similarly positioned around graft fixation member 100 and into channels 108 so that the continuous loop of suture 30 wraps around intermediate member 104 of graft fixation member 100. Both bights 32, 34 are wrapped around intermediate member 104 so that the closed-loop suture 30 does not interfere with the positioning of strands of suture 42 into openings 118.

Lengths of suture 42 and 44, shown in FIG. 6, are chosen to capture closed-loop suture 30 within graft fixation member 100 during the ACL reconstruction described below. In one example, lengths of polyester closure tape could be used instead of sutures 42, 44. End 43 of suture 42 is passed through opening 118 (FIG. 2) in either arm 106 of pair of arms 106A and over closed-loop suture 30. End 43 is then passed through opening 118 in the corresponding arm 106 of pair of arms 106A thereby capturing closed-loop suture 30 within graft fixation member 100. It is important that suture 42 passes over, and not under, closed-loop suture 30. Allowing suture 42 to pass under closed-loop 30 would not capture closed-loop 30 within graft fixation member 100. Similarly, end 45 of suture 44 is passed through opening 118 in either arm 106 of a pair of arms 106B and over closed-loop suture 30. End 45 is then passed through opening 118 in the corresponding arm 106 of pair of arms 106B thereby further capturing closed-loop suture 30 within graft fixation member 100. It is important that suture 44 passes over and not under closed-loop suture 30. As was the case with suture 42, passing suture 44 under closed-loop 30 does not capture closed-loop 30 within graft fixation member 100. In this manner, closed-loop suture 30 is captured twice within fixation member 100.

Figure 7:
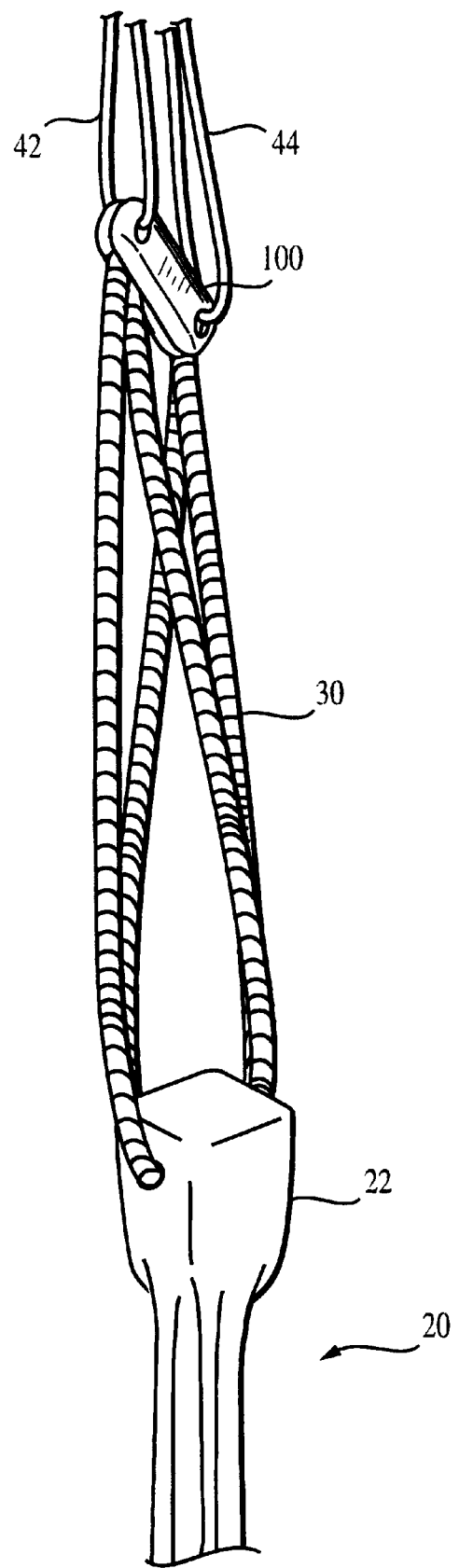
FIG. 7 shows the graft fixation member positioned for implantation.

Referring to FIG. 7, pulling to sutures 42 and 44 removes slack from closed-loop suture 30 and positions graft fixation member 100 to pass through tibial channel 16, femoral channel 14, and passing channel 18 (FIG. 2).

Figure 8:
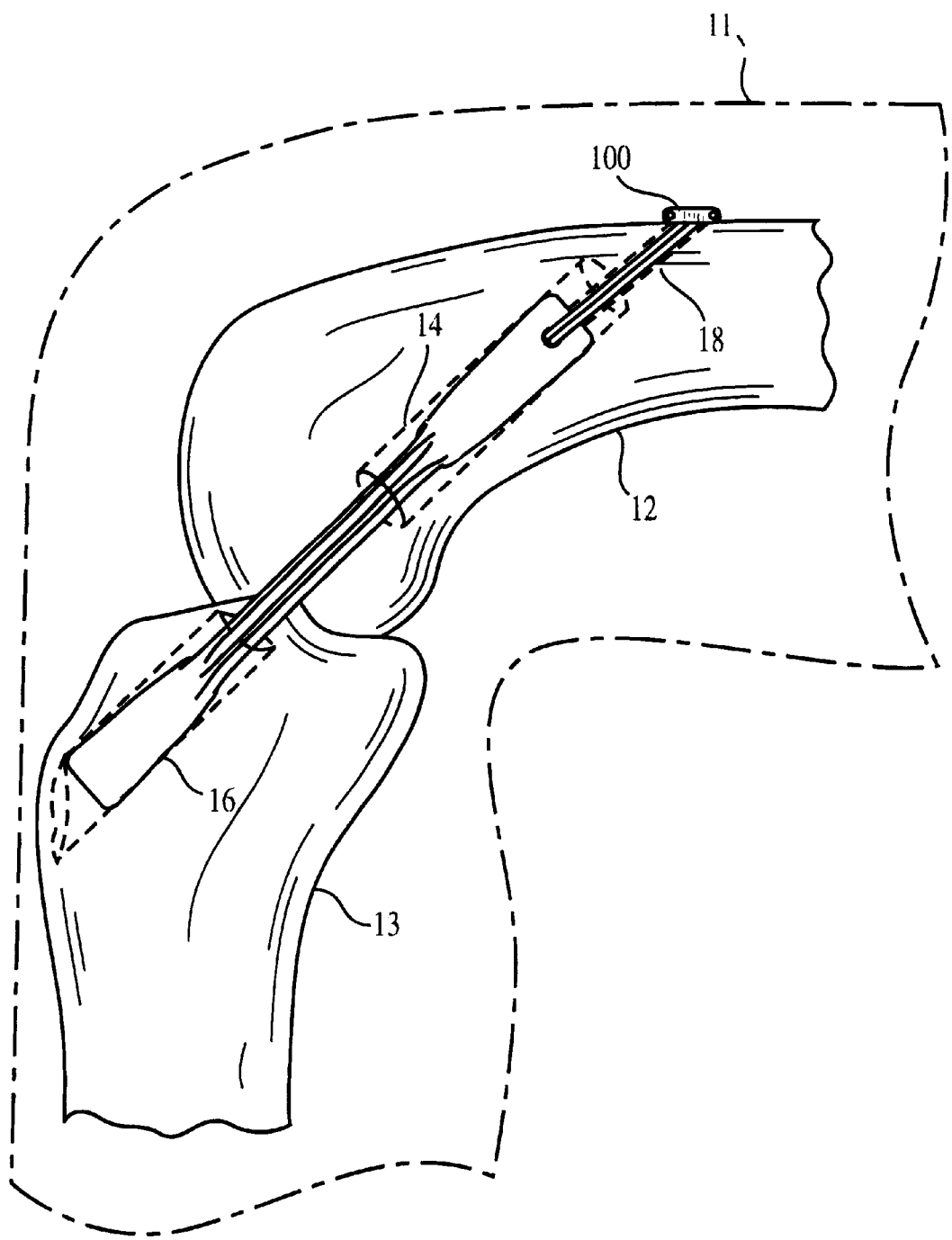
FIG. 8 shows the tissue graft implanted in a knee and secured at one end by the graft fixation member.

An example of a procedure for placing graft fixation member 100 in the position shown in FIG. 8 follows with reference to FIG. 1. Drilling procedures are performed to provide the appropriately sized tibial channel 16 extending through tibia 13 and femoral passage 14 in the manner described in the '301 patent. Sutures 42 and 44 are removably attached to passing pin 50. Passing pin 50 (FIG. 1) is then inserted through an incision below the knee and advanced through tibial channel 16, femoral channel 14, passing channel 18, the quadriceps tissue, and skin 11 of the thigh. Ends of sutures 42 and 44 are withdrawn beyond the skin 11 using passing pin 50.

The surgeon then pulls graft fixation member 100 by pulling suture 42 through tibial channel 16, femoral channel 14, and passing channel 18 to position graft fixation member 100. It is important that the surgeon keep closed-loop suture 30 captured within channel 108B by taking up any slack in suture 44 while advancing graft fixation member 100 through passing channel 18 with suture 42. However, the surgeon must be careful not to apply too much tension on suture 44 in relation to the tension on suture 42 or graft fixation member 100 will wedge within tibial channel 16, femoral channel 14, or passing channel 18. Once fixation member 100 has been pulled through passing channel 18, the surgeon positions fixation member 100 transversely to passing channel 18 and across opening 19. Fixation member 100 is secured against femur 12 by attaching tissue graft 20 to tibia 13 and tensioning tissue graft 20 and closed-loop suture 30 according to methods described in the '301 patent.

Other embodiments are within the scope of the claims.

Figure 9:
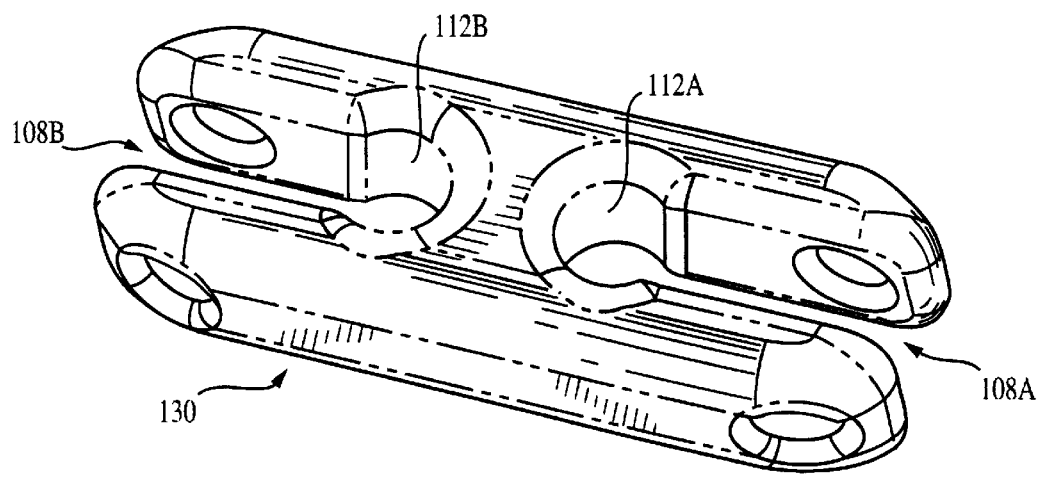
FIG. 9 shows an alternative example of a graft fixation member.

For example, referring to FIG. 9, cylindrical portions 112A and 112B of graft fixation member 130 may have a diameter that is larger than the width of channels 108A and 108B, respectively. In one example, portions 112A, 112B have a diameter of about 0.078 inches and channels 108A, 108B have a width of about 0.05 inches. As the diameter of portions 112A and 112B increases, graft fixation member 100 can accommodate a thicker closed-loop suture (i.e., having an increased number of windings). The width of channels 108A and 108B do not constrain the sue of thicker closed-loop sutures because a closed-loop suture may be flattened to pass through channels 108A and 108B.

Figure 10:
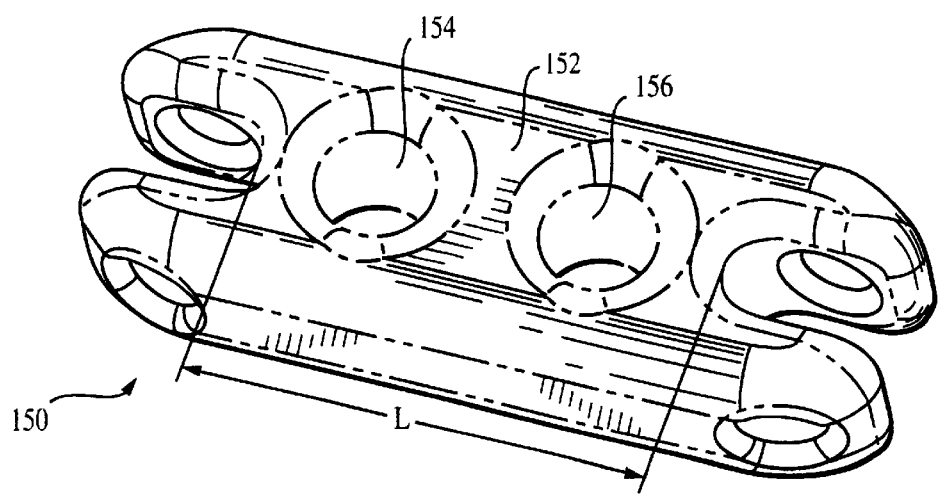
FIG. 10 shows a second alternative example of a graft fixation member.
Figure 11:
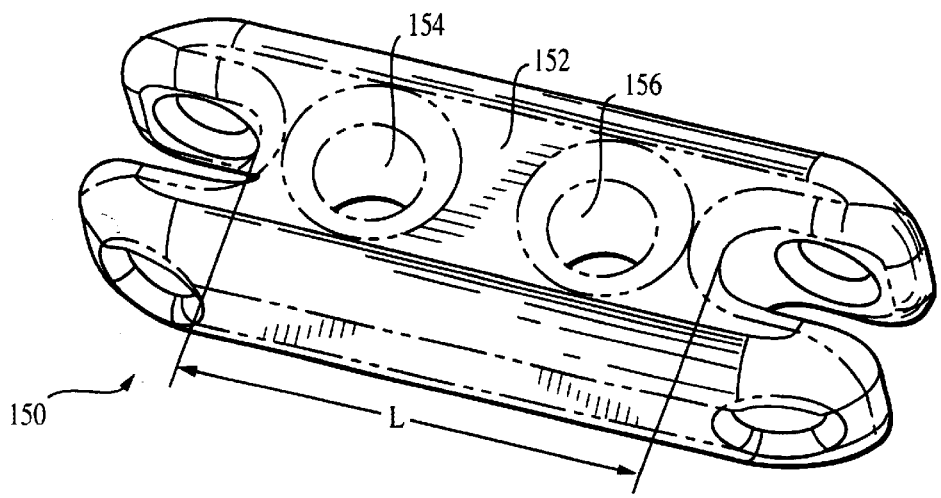
FIG. 11 shows a third alternative example of a graft fixation member.

Referring to FIGS. 10 and 11, intermediate portion 152 of fixation member 150 has a length (L) and defines openings 154, 156 extending through intermediate portion 152. In the example shown in FIG. 10, intermediate portion has a length of about 0.268 inches and openings 154, 156 are about 0.078 inches in diameter. In the example shown in FIG. 11, intermediate portion has a length of about 0.232 inches and openings 154, 156 are about 0.06 inches in diameter. A closed-loop suture 30 may be attached to fixation member 150 using the method described in the '079 application. Alternatively a first and second end of a length of suture or closure tape may be threaded through openings 154, 156, respectively, and tied together. Increasing length L adds material to intermediate portion 152 and increases the strength of graft fixation member 150.

Figure 12:
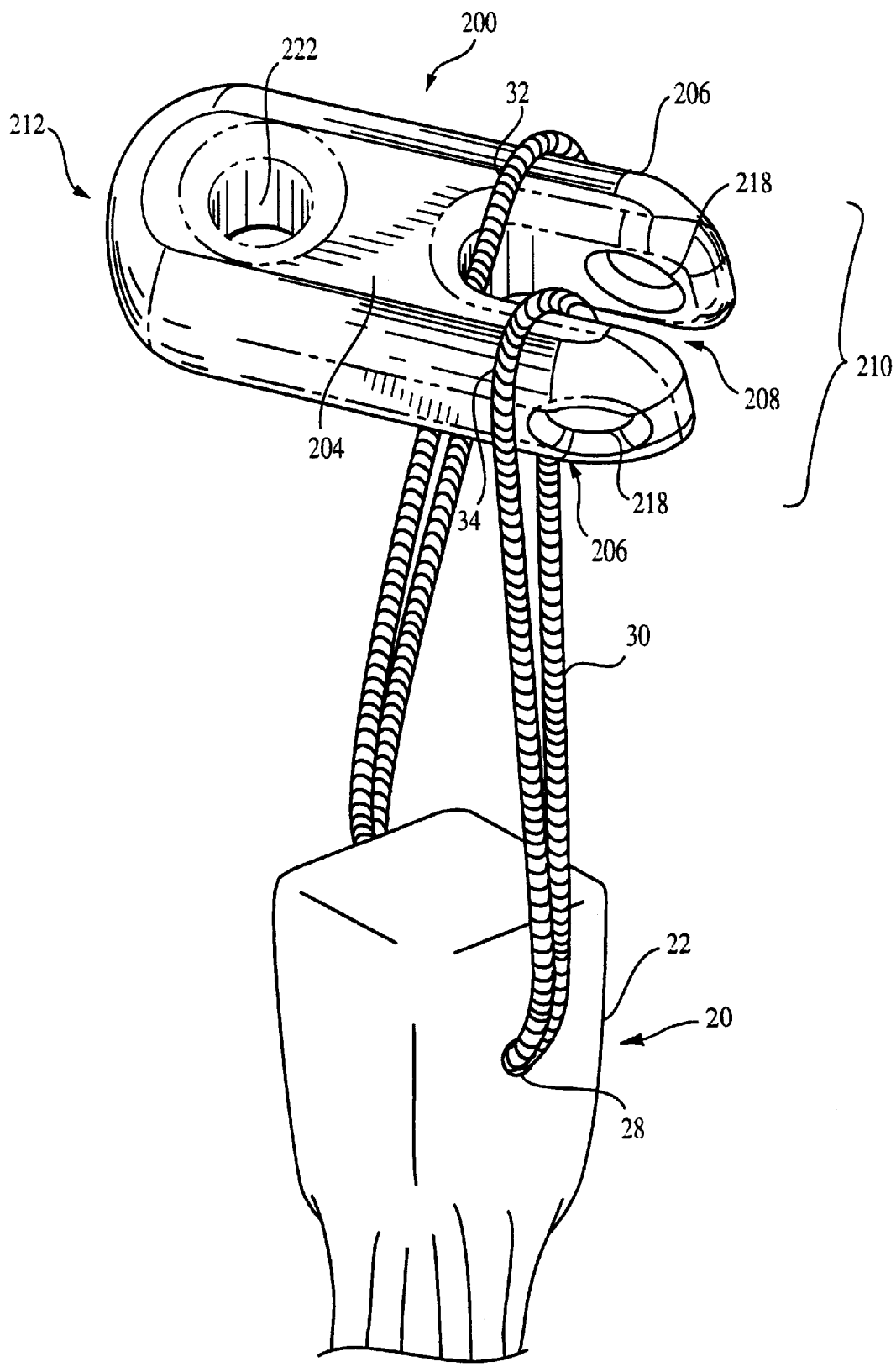
FIG. 12 shows a fourth alternative example of a graft fixation member and a method for capturing first and second portions of a closed-loop suture.

Referring to FIG. 12, fixation member 200 has only one pair of arms 206 extending from intermediate portion 204 and forming a single channel 208 at end 210. Arms 206 include cylindrical openings for capturing closed-loop suture 30 and positioning fixation member 200. End 212 is closed and rounded to facilitate passing fixation member 200 through bone passages during the positioning and attachment of tissue gaft 20. End 212 may include opening 222 through which a strand of suture may be threaded to improve a surgeon's ability to position fixation member 200 during an ACL reconstruction procedure.

Closed-loop suture 30 is captured in fixation member 200 by positioning arms 206 through bights 32, 34 and threading suture 42 (not shown) through a first opening 218, over bights 32, 34, and through the second opening 218. In one example, bight 32 is positioned on a first arm 206 and bight 34 is positioned on a second arm 206. In another example, bights 32, 34 could be positioned on the same arm.

Figure 13:
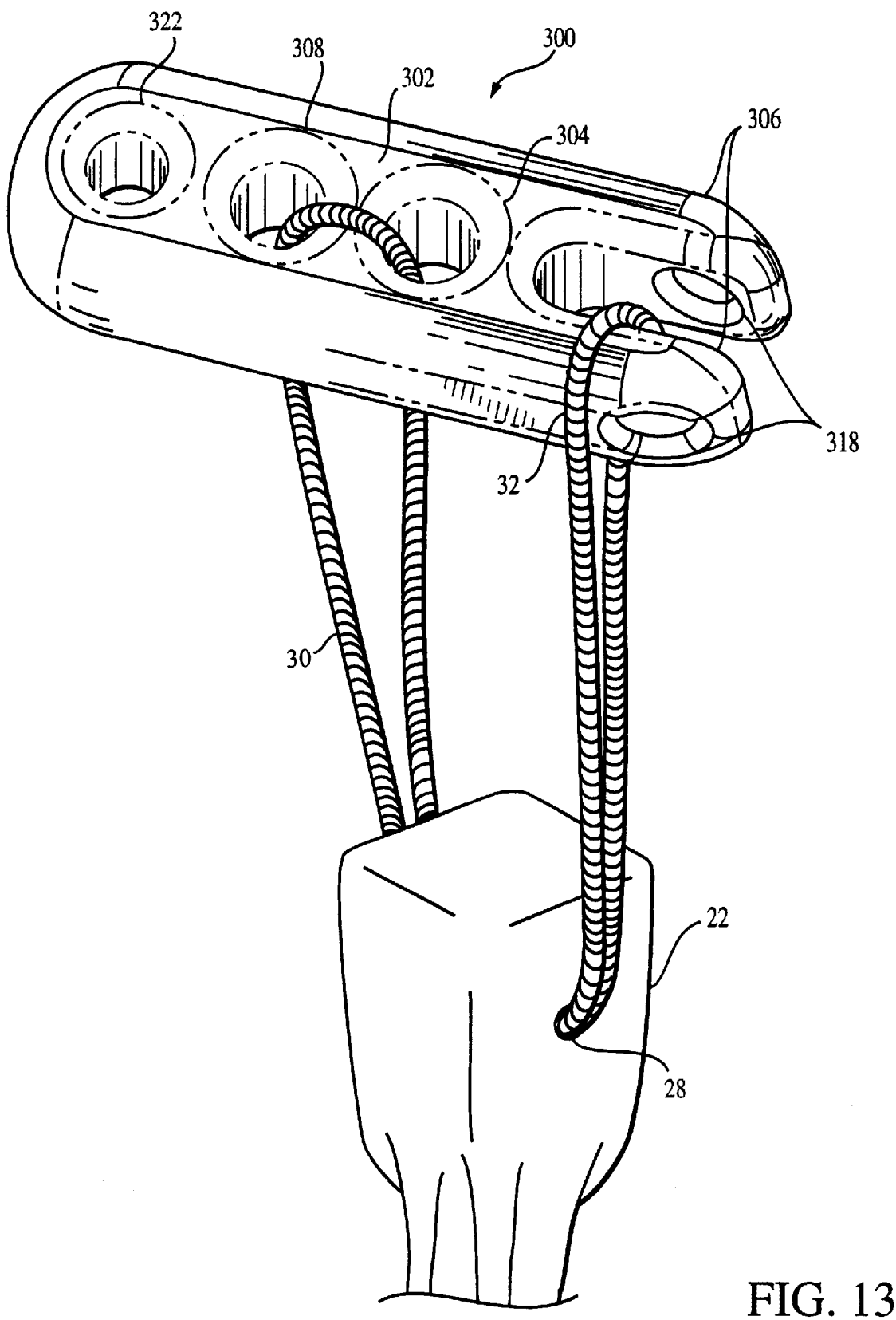
FIG. 13 shows a fifth alternative example of a graft fixation member and a method of attaching it to a tissue graft using a closed-loop suture.

Referring to FIG. 13., fixation member 300 includes openings 304, 308 in intermediate portion 302 and a pair of arms 306 with an opening 318 through each arm. Closed-loop suture 30 is formed in openings 304, 308 according to the method described in the '079 application. Alternatively, a piece of suture or closure tape could be tied into a loop passing through openings 304, 308 as described above. After forming bight 32 by passing closed-loop suture 30 into opening 28 in bone block 22, closed-loop suture 30 is captured by fixation member 300 by positioning either arm 306 through bight 32 and threading a strand of suture (not shown) through openings 318, as described above.

Figure 14:
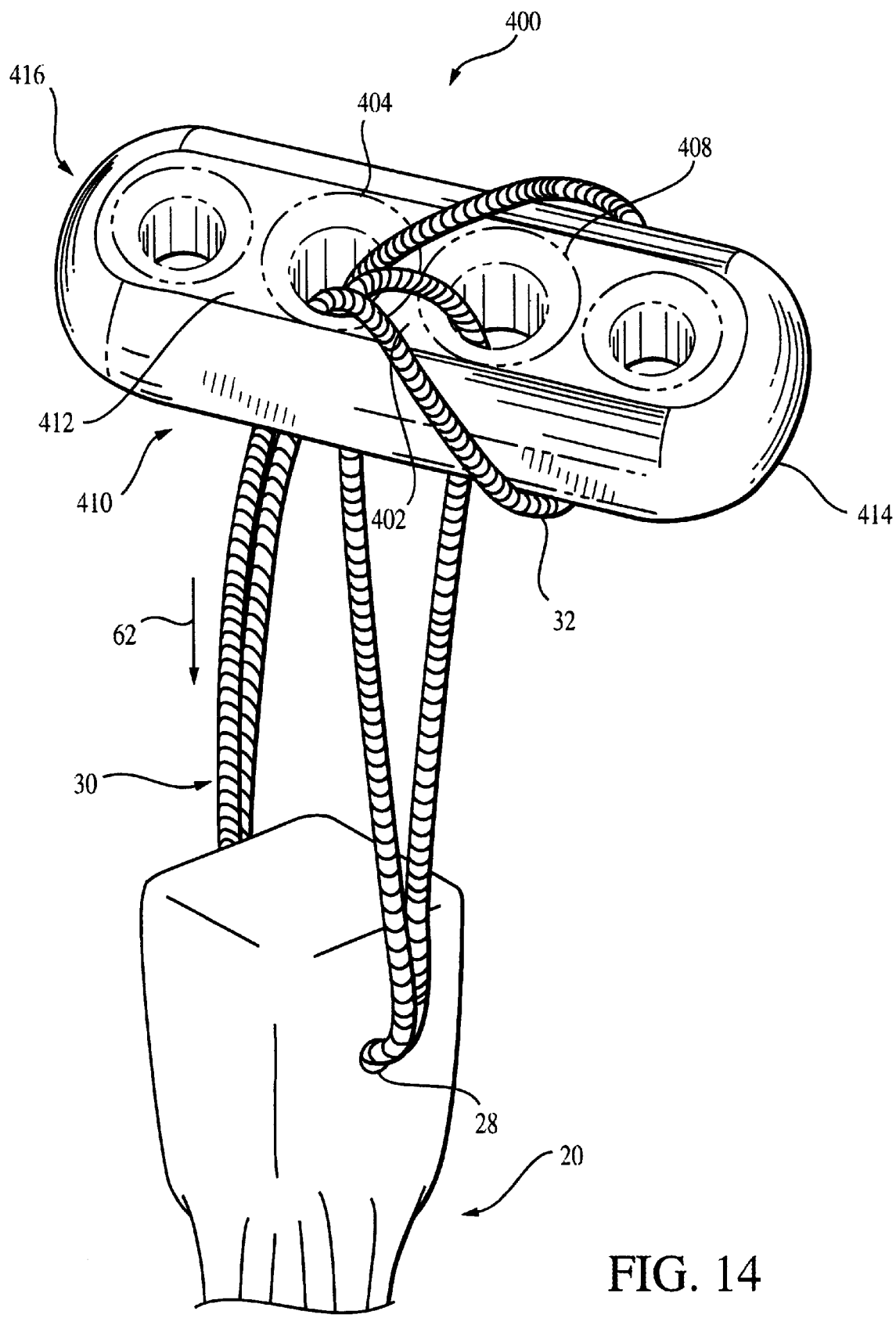
FIG. 14 shows a sixth alternative example of a graft fixation member and method of attaching it to a tissue graft using a closed loop suture.

Referring to FIG. 14 fixation member 400 is similar in size to fixation member 100, described above, and has a four opening configuration described in the '301 and '894 patents. Closed-loop suture 30 has been formed in openings 404, 408 of fixation member 400 according to the method set forth in the '079 patent, thereby capturing a first portion of closed-loop suture 30.

Tissue graft 20 is attached to fixation member 400 by passing closed-loop suture 30 into opening 28, thereby forming bight 32, and capturing a second portion of closed-loop suture 30 with fixation member 400. In the example of FIG. 14, bight 32 is inserted into opening 404 at bottom side 412 of member 400 and out of opening 404 at top side 412 until bight 32 can extend past end 414 of fixation member 400. End 414 is passed through bight 32. Bight 32 is pulled in direction 62 until bight 32 tightens around fixation member 400, thereby capturing a second portion of closed-loop suture 30. In another example, end 416 could be passed through bight 32 instead of end 414.

Figure 16:
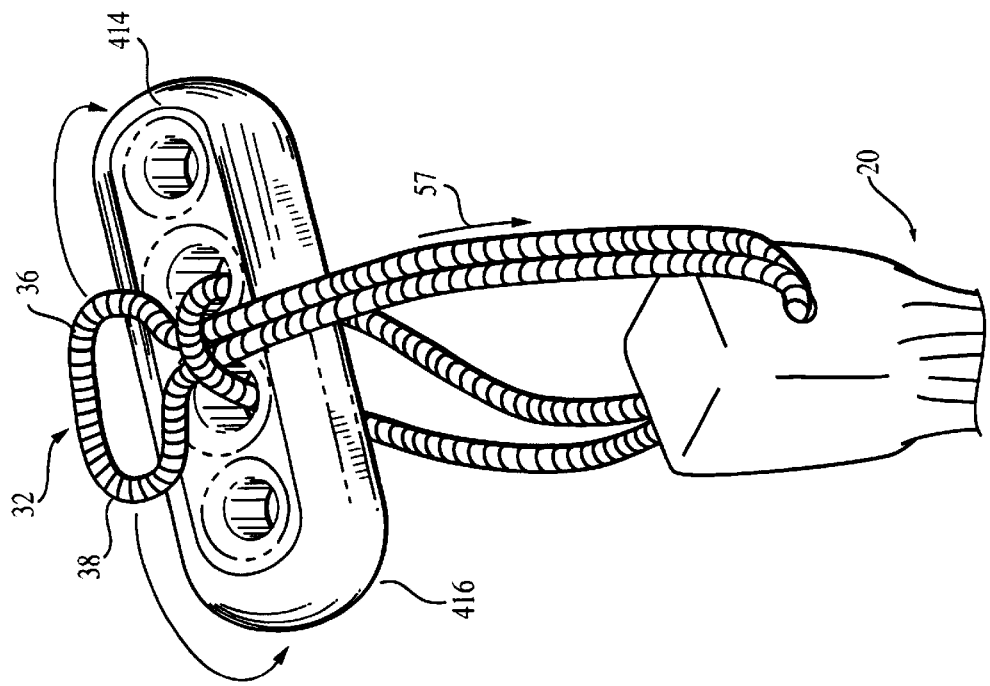
FIGS. 15–17 show an alternative method for attaching a graft fixation member to a tissue graft using a closed-loop suture.
Figure 15:
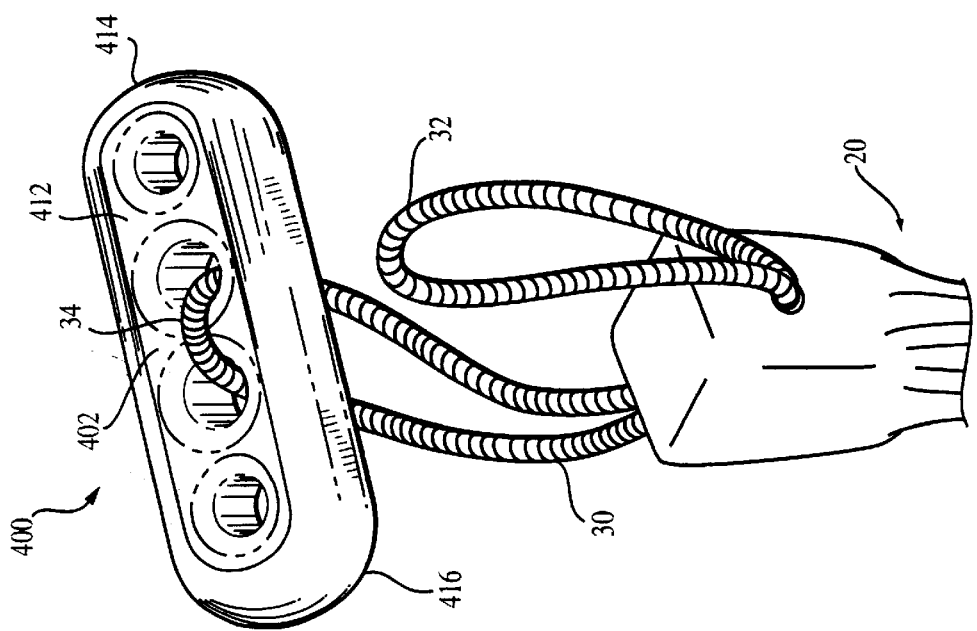
Figure 17:
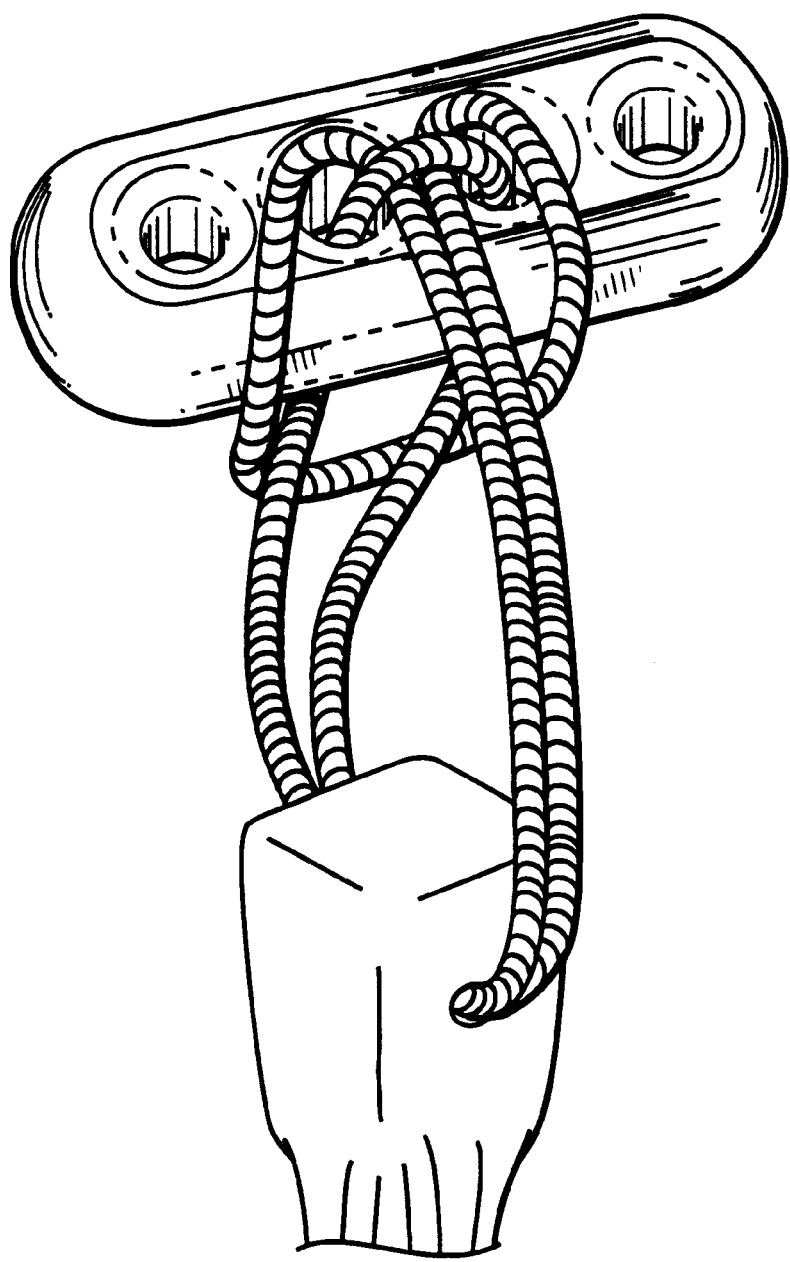

Referring to FIGS. 15–17, another method by which tissue graft 20 could be attached to fixation member 400 follows. Closed-loop suture 30 has been formed around intermediate portion 402 of fixation member 400 according to the method described in the '079 application and a portion of closed-loop suture 30 is passed into opening 28, as described above, to form bights 32, 34. Bight 32 is passed through bight 34 on top side 412 of fixation member 400 about 1 inch of closed-loop suture 30 has been pulled through bight 34. Bight 32 is then opened to form bights 36, 38 and end 414 is then passed through bight 36 and bight 38 is passed through end 416. Closed-loop suture 30 is tensioned in direction 57, removing slack from closed-loop suture 30 and attaching it to fixation member 400.

Figure 18D:
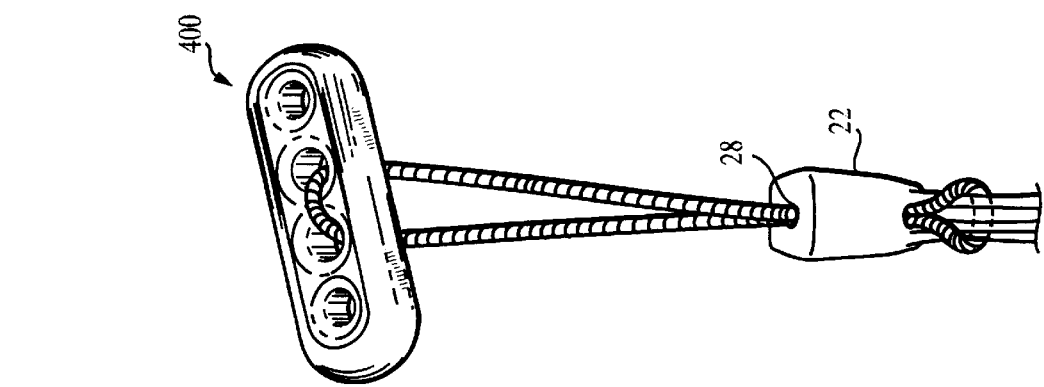
FIGS. 18A–18D show a second alternative method for attaching a graft fixation member to a tissue graft using a closed-loop suture.
Figure 18C:
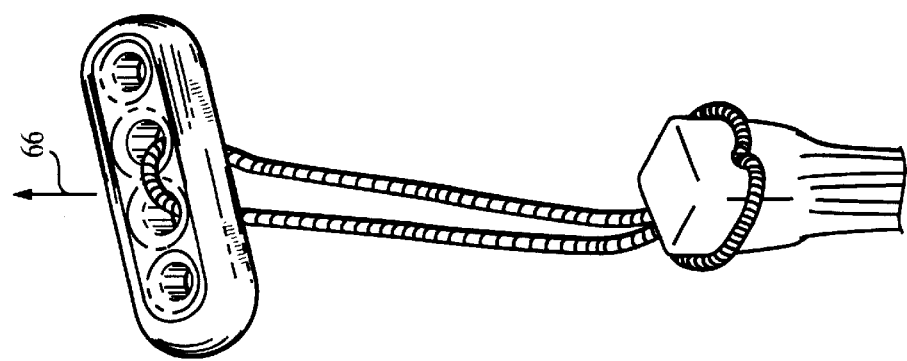
Figure 18B:
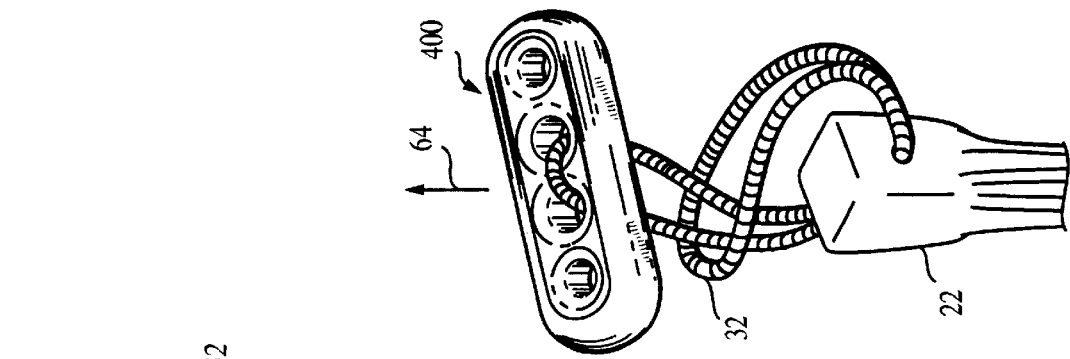
Figure 18A:
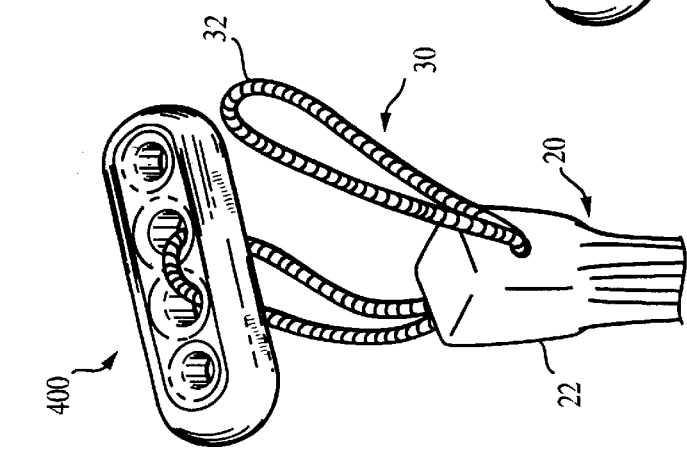

Referring to FIGS. 18A–D, tissue graft 20 could be attached to fixation member 400 by capturing closed-loop suture 30 only once at fixation member 400. For example, closed-loop 30 is passed through opening 28 (not shown) in bone block 22 to form bight 32 (FIG. 18A). Fixation member 400 is then passed through bight 32 (FIG. 18B) and pulled in direction 66, away from tissue graft 20, thereby causing bight 32 to tighten around bone block 22, as best seen in FIG. 18C. In another embodiment, opening 28 is formed along the length of block 22 (FIG. 18D) instead of transversely, as shown in examples above. Fixation member 400 is attached to tissue graft 20 in the same manner as described above despite the longitudinal orientation of opening 28.

Figure 19:
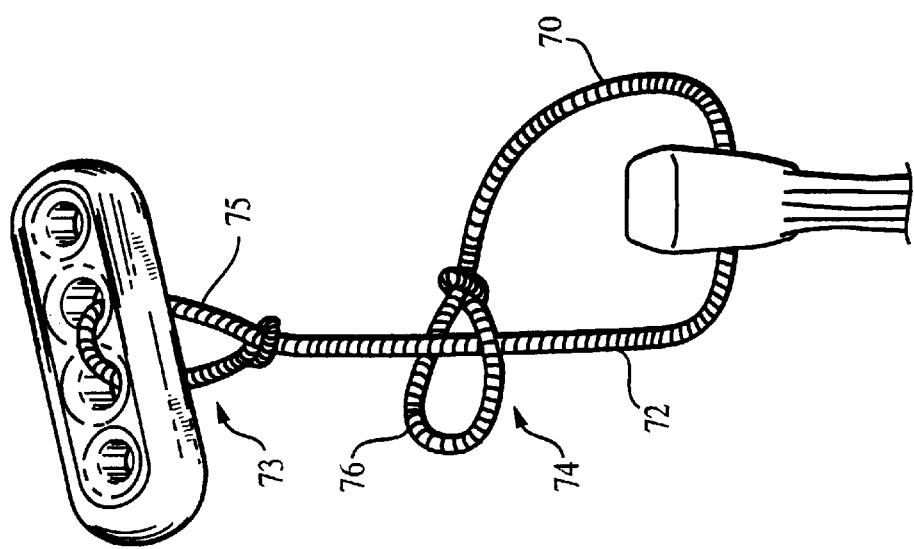
FIG. 19 shows an alternative example of a closed loop suture.

Referring to FIG. 19, closed-loop suture 70 is a suture 72 having opposing ends 73 and 74. In one example, suture 72 could have a total length of about 1.5 inches. End 73 includes a loop 75 and end 74 includes a loop 76. Loops 75, 76 have a length of about 0.3 inches or less.

Figure 20:
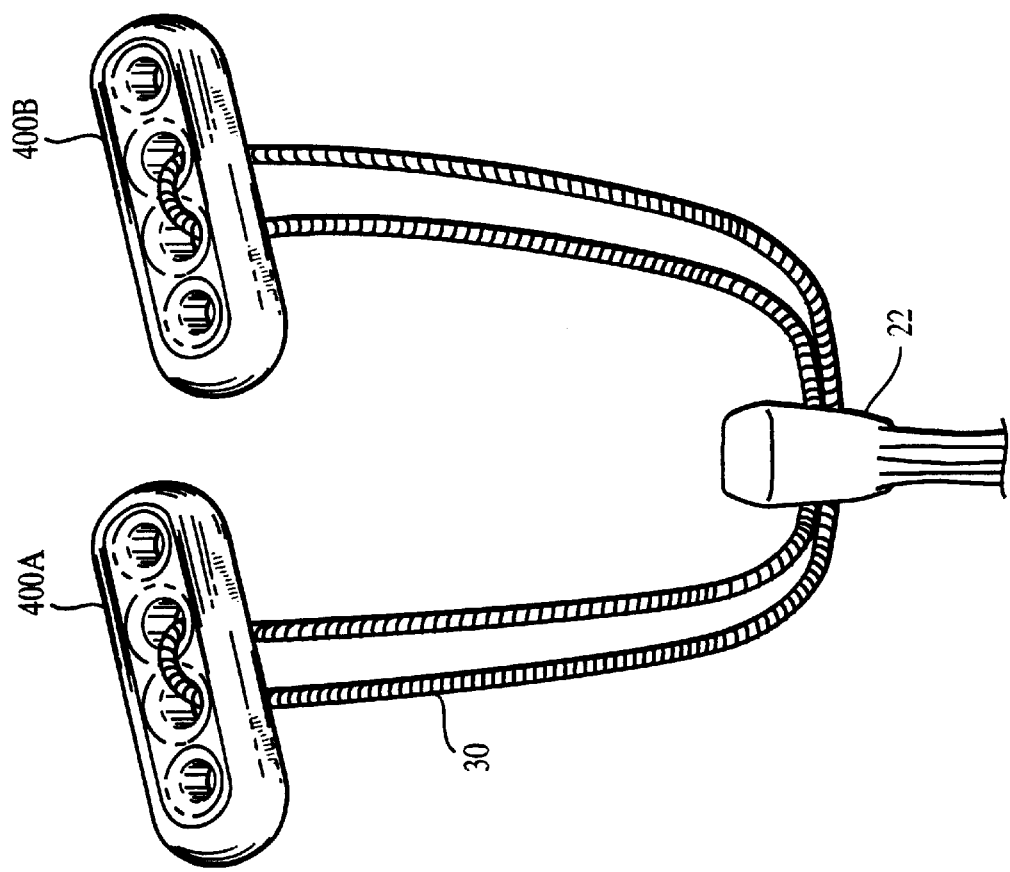
FIG. 20 shows a third alternative method for attaching a graft fixation member to a tissue graft using a closed-loop suture.

Referring to FIG. 20, a closed-loop suture 30 is formed in more than one fixation member 400. In one example, closed-loop suture 30 is formed in fixation member 400A and 400B. When closed-loop suture 30 is formed by the method disclosed in the '079 application, opening 28 (not shown) in bone block 22 is sized to permit fixation member 400 to pass through opening 28. When closed-loop suture 30 is formed by tying a length of suture or closure tape, opening 28 need only be sized to accommodate the suture or tape. During implantation, a surgeon could use sutures (e.g., suture 42, 44) to pass fixation members 400A, 400B through passing channel 18 at the same time or pass them individually.

Other embodiments include an alternative approach for securing a tissue graft within a bone passage using fixation member 100. Specifically, the fixation member 100 and tissue graft 20 could be pulled first through a femoral channel and then through a tibial channel.

Although the tissue graft described above has at least one bone block, other types of grafts may be attached to graft fixation member including ligament augmentation devices (LAD) formed of artificial ligament material to which the tissue is sutured.

In general, graft fixation member 100 can be used to secure any suitable kinds of grafts, such as alografts, autografts, and xenografts and can be used in surgical soft tissue reconstruction procedures other than those related to ACL reconstruction.

Accordingly, other embodiments are within the scope of the following claims.

What is claimed is:

1. A method of securing a tissue graft within a bone passage comprising:
  providing a graft fixation member comprising a closed-loop having a pair of opposing loop sections;

capturing a first loop section of the closed-loop within the fixation member passing an opposing second loop section of the closed loop through an opening in the tissue graft; and securing the second loop section of the closed loop to the fixation member.

2. The method of claim 1 further comprising forming the opening in the tissue graft.

3. The method of claim 2 wherein the opening is formed in a bone block of the tissue graft.

4. The method of claim 2 wherein the opening is formed in a tendon of the tissue graft.

5. The method of claim 1 further comprising passing the fixation member through the bone passage.

6. The method of claim 5 wherein passing the fixation member through the bone passage comprises first passing the fixation member through a bone passage in a tibia and then through a bone passage in a femur.

7. The method of claim 5 wherein passing the fixation member through the bone passage comprises first passing the fixation member through a bone passage in a femur and then through a bone passage in a tibia.

8. The method of claim 1 further comprising positioning the fixation member to pass through the bone passage using a suture.

9. The method of claim 1 further comprising positioning the fixation member to pass through the bone passage using closure tape.

10. A method of securing a tissue graft within a bone passage comprising:

providing a graft fixation member comprising a closed loop having a pair of opposing loop sections;

capturing a first loop section of the closed loop within the fixation member;

forming a bight in the closed loop by passing an opposing second loop section of the of the closed loop through an opening in the tissue graft; and passing the fixation member and the first loop section through the bight in the closed loop to capture the tissue graft.

11. The method of claim 10 further comprising forming the opening in the tissue graft.

12. The method of claim 11 wherein the opening is formed in a bone block of the tissue graft.

13. The method of claim 11 wherein the opening is formed in a tendon of the tissue graft.

14. The method of claim 10 further comprising passing the fixation member through the bone passage.

15. The method of claim 14 wherein passing the fixation member through the bone passage comprises first passing the fixation member through a bone passage in a tibia and then through a bone passage in a femur.

16. The method of claim 14 wherein passing the fixation member through the bone passage comprises first passing the fixation member through a bone passage in a femur and then through a bone passage in a tibia.

17. The method of claim 10 further comprising positioning the fixation member to pass through the bone passage using a suture.

18. The method of claim 10 further comprising positioning the fixation member to pass through the bone passage using closure tape.

19. A method of securing a tissue graft within a bone passage comprising:

providing a first graft fixation member and a second graft fixation member and a closed loop having a pair of opposing loop sections;

capturing a first loop section of the closed loop within the first graft fixation member;

passing an opposing second loop section through an opening in the tissue graft; and capturing the second loop section of the closed loop of suture within the second graft fixation member.

20. The method of claim 19 further comprising forming the opening in the tissue graft.

21. The method of claim 20 wherein the opening is formed in a bone block of the tissue graft.

22. The method of claim 20 wherein the opening is formed in a tendon of the tissue graft.

23. The method of claim 19 wherein the second loop section is captured within the second fixation member before the second loop section is passed through the opening in the tissue graft.

24. The method of claim 23 wherein passing the second loop section through the opening in the tissue graft comprises passing the second fixation member through the opening.

25. A device for securing a tissue graft within a passage within a bone comprising:

a member comprising an intermediate portion and an end portion;

said end portion comprising a pair of arms extending from the intermediate portion and defining an open channel at said end portion; and each arm comprising an opening extending from a first side of the arm to a second side of the arm, the opening being sized to accommodate a strand of suture.

26. The device of claim 25 wherein one or more openings pass through the intermediate portion of the member.

27. The device of claim 26 wherein the openings are cylindrical.

28. The device of claim 25 wherein the opening in each arm is cylindrical.

29. The device of claim 25 wherein the openings in each pair of arms occupy different positions on a common axis.

30. The device of claim 29 wherein the axis is transverse to the member.

31. The device of claim 25 wherein the pair of arms define a cylindrical portion of the channel having a diameter equal to the width of the channel.

32. The device of claim 25 wherein each pair of arms define a cylindrical portion of the channel having a diameter greater than the width of the channel.

33. The device of claim 25 wherein the arms are shaped to pass through bone passage.

34. The device of claim 25 wherein the member is sized to pass through a bone passage.

35. The device of claim 25 wherein the member comprises a bio-compatible material.

36. The device of claim 25 wherein the member comprises titanium.

37. The device of claim 25 wherein the member comprises a bio-absorbable material.

* * * * *